US00PP08482P

United States Patent [19]

Laver

[11] Patent Number: Plant 8,482

[45] Date of Patent: Dec. 7, 1993

[54] MINIATURE ROSE PLANT NAMED 'LAVPUP'

[75] Inventor: Keith Laver, Ontario, Canada

[73] Assignee: The Conard-Pyle Company, West Grove, Pa.

[21] Appl. No.: 965,715

[22] Filed: Oct. 23, 1992

[51] Int. Cl.[5] ..... A01H 5/00

[52] U.S. Cl. ..... Plt./10

[58] Field of Search ..... Plt. 7.1, 10

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which abundantly forms in uniform flushes attractive long-lasting double Tyrian Purple blossoms wherein the coloration is extremely stable. The plant is very compact and very bushy and the vegetation is vigorous. The blooms exhibit an excellent shape (as illustrated). The plant is well adapted to greenhouse forcing while grown in small containers, and is particularly well suited for use as a flowering pot plant when grown indoors or outdoors. Additionally, the plant is not particularly affected by cryptogamic diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the JUNE Laver Variety (non-patented in the United States) by the PAINTED DOLL variety (non-patented in the United States). The male parent (i.e., the pollen parent) of the new variety was the SPRINGWOOD PURPLE variety (non-patented in the United States). The parentage of the new variety can be summarized as follows:

(JUNE LAVER × PAINTED DOLL) × SPRINGWOOD PURPLE.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms in abundance in uniform flushes attractive double long-lasting blossoms having an excellent shape which are of a stable Tyrian Purple coloration,
(b) exhibits a very compact and very bushy growth habit,
(c) is well adapted to greenhouse forcing when grown in small containers,
(d) is particularly suited for growth as a flowering pot plant when grown indoors and outdoors, and
(e) is not particularly affected by cryptogamic diseases.

The new variety well meets the needs of the horticultural industry. It is particularly well-suited for use as attractive ornamentation as a flowering pot plant when grown indoors or outdoors. The flowering is very uniform and the shape of the bloom is excellent.

The new variety has been found to undergo asexual propagation at West Grove, Pa., U.S.A., by a number of routes, including budding, grafting, cuttage, etc. The characteristics of the new variety have been found to be strictly transmissible by such asexual propagation from one generation to another.

The new variety has been named the LAVPUP variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were eighteen months of age and were observed during September while growing on their own roots in the greenhouse at West Grove, Pa., U.S.A.

At the left (top) is shown a specimen of a young shoot. At the left (middle) is shown a specimen of a main stem. At the top row (middle) are shown specimens of three buds before the sepals open. To the right of the three buds are shown specimens of a receptacle showing the arrangement of the stamens and pistils and of a receptacle showing the arrangement of the pistils (stamens removed). At the second row (middle) are shown specimens of two buds as the petals begin to open. At the second row (right) are shown specimens of two flowers during the early stage of opening. At the third row are shown specimens of open flowers with the obverse being illustrated at the right and the reverse being illustrated at the middle. At the fourth row are shown specimens of fully open flowers with the obverse being illustrated at the middle and the reverse being illustrated at the right. Across the bottom row are shown in pairs specimens of leaves with three, five, and seven leaflets with the upper surface being illustrated on the left of each pair and the under surface being illustrated on the right of each pair.

DETAILED DESCRIPTION

The chart used in the identification of the colors is that of The Royal Horticultural Society (R.H.S. Colour Chart). The terminology which sometimes precedes reference to the chart has been added to indicate the corresponding colors in common terms. The description is based on eighteen month old specimens of the new variety which were observed during September while growing on their own roots in the greenhouse at West Grove, Pa., U.S.A.

Class: Miniature.

Plant:

*Height.*—Approximately 30 cm. on average when grown outdoors or in a one-gallon container on its own roots.

*Habit.*—Very compact and very bushy.

Branches:

*Color.*—Young stems: reddish green. Adult wood: Green Group 138A, and sometimes slightly stained with reddish coloration.

*Thorns.*—Size: large. Quantity: average. Color: reddish and yellowish at the tip.

Leaves:

*Petioles.*—Upper surface: striped, reddish green on young foliage and light green on mature foliate with glandular edges. Under surface: medium green with some reddish prickles.

*Leaflets.*—Number: 3, 5, and 7. Sometimes the lower leaflet pair is incomplete. Shape: spear-shaped. Serration: single and regular. Texture: consistent. General appearance: bright, dense, semi-matte foliage. Color (young foliage): upper surface: light green, Green Group 143C. under surface: light green, Yellow-Green Group 146D and stained with light reddish coloration. Color (adult foliage): upper surface: dark green, Green Group 137A. under surface: medium green, Green Group 138B.

Inflorescence:

*Number of flowers.*—Approximately 1 to 5 blooms per stem.

*Peduncle.*—Light green, fairly straight and rigid, bears many prickles, reddish in coloration on young stems and turning to light green on mature blooms, its length is approximately 1.5 cm. on average.

*Sepals.*—Upper surface: tomentose and greenish in coloration. Under surface: light green, bear numerous tiny reddish appendiculate glands, and sometimes end in a leaf-like appendix.

*Buds.*—Shape: rounded. Length: approximately 1 cm. on average. Size: small. Color upon opening: Upper surface: Ruby Red, Red-Purple Group 64A, and turning to Indian Lake, Red-Purple Group 58A, near the center of the petal. Under surface: Ruby Red, Red-Purple Group 61B.

*Flower.*—Form: cup-like, and double Diameter: approximately 3.5 to 4 cm. on average when fully open. Color (when opening begins): Upper surface: Indian Lake, Red-Purple Group 58A, turning to Tyrian Purple, Red-Purple Group 57A, near the center of the petal. Under surface: Tyrian Purple, Red-Purple Group 57A. Color (when blooming): Upper surface: Tyrian Purple, Red-Purple Group 57A. Under surface: Tyrian Purple, Red-Purple Group 57A, and turning to Rose Bengal, Red-Purple Group 57C, near the base of the petal. Color (at end of blooming): Upper surface: Tyrian Purple, Red-Purple Group 57A, and light Rose Bengal, Red-Purple Group 57D, on the outer petals. At this stage the pistils and stamens are clearly visible. Under surface: Tyrian Purple, Red-Purple Group 57A, turning to Rose Red, Red-Purple Group 58B, near the center, and light Rose Bengal, Red-Purple Group 57D, on the outer petals. Fragrance: none. Lasting quality: very long on the plant. Petal number: approximately 18 to 20 on average. Petal shape: rounded. Petal texture: consistent. Petal drop: very good. Anthers: normal, yellow in coloration, and fairly wide. Stamen number: approximately 105 to 115 on average. Filaments: normal, yellow in coloration, and of irregular heights. Pistil number: approximately 25 to 30 on average. Stigmas: normal, and whitish. Styles: tomentose, whitish, twisted near the base, and irregular in height. Receptacle: light green, smooth, and funnel-shaped.

Development:

*Vegetation.*—Vigorous.

*Blooming.*—Very abundant in flushes.

*Aptitude to bear fruits.*—None.

Resistance to diseases.—Good.

I claim:

1. A new and distinct variety of Miniature rose plant characterized by the following combination of characteristics:

(a) forms in abundance in uniform flushes attractive double long-lasting blossoms having an excellent shape which are of a stable Tyrian Purple coloration, (b) exhibits a very compact and very bushy growth habit, (c) is well adapted to greenhouse forcing when grown in small containers, (d) is particularly suited for growth as a flowering pot plant when grown indoors and outdoors, and (e) is not particularly affected by cryptogamic diseases; substantially as herein shown and described.

* * * * *

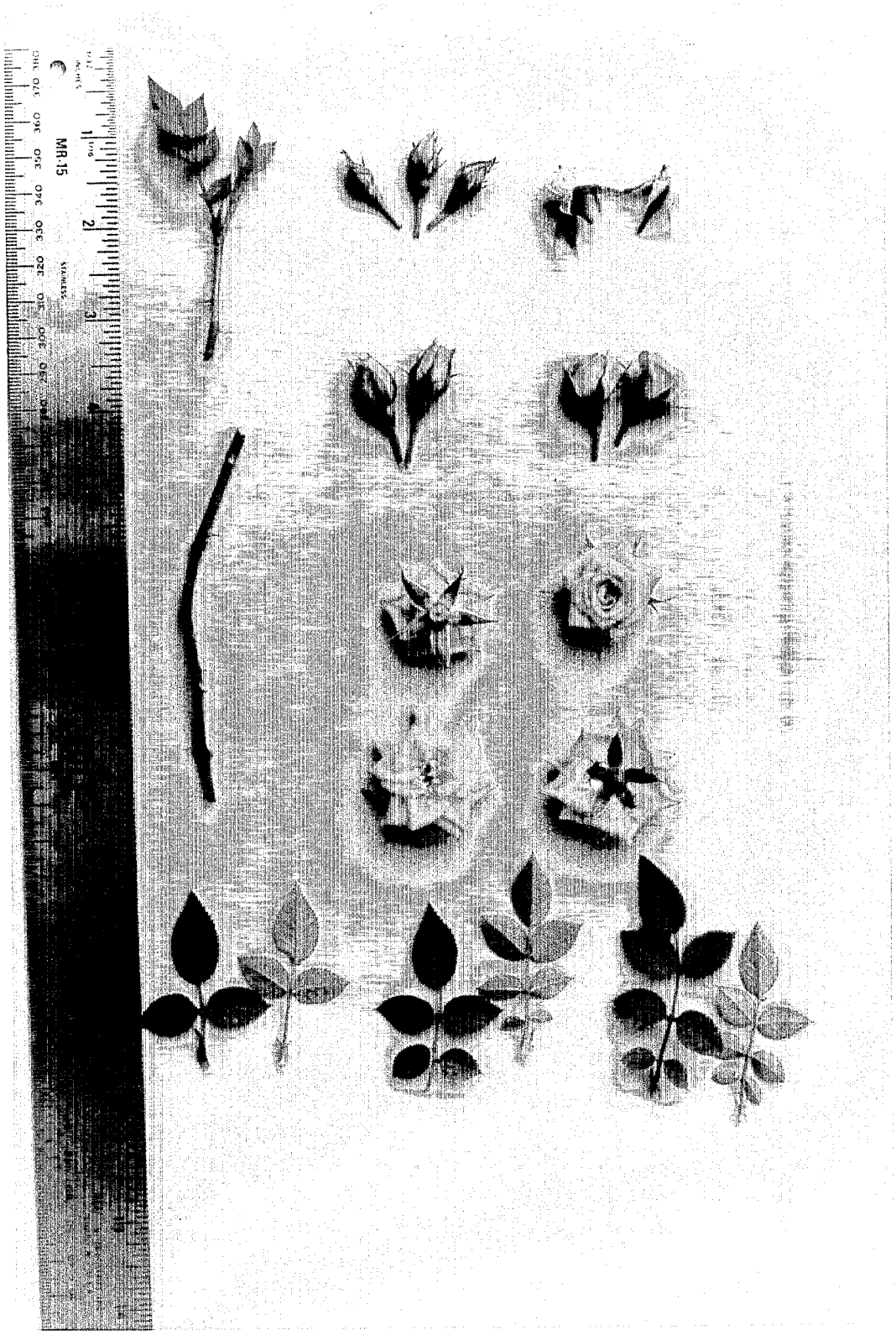
MR-15